United States Patent [19]

Rivers

[11] Patent Number: 5,247,087
[45] Date of Patent: Sep. 21, 1993

[54] EPOXY MODIFIED WATER CLARIFIERS
[75] Inventor: Gordon T. Rivers, Houston, Tex.
[73] Assignee: Baker Hughes Incorporated, Houston, Tex.
[21] Appl. No.: 882,663
[22] Filed: May 13, 1992
[51] Int. Cl.$^5$ .................. C07D 241/04; C07D 295/00; C07D 333/00; B01D 17/04
[52] U.S. Cl. .................. 544/357; 544/389; 544/401; 210/708; 210/727; 210/728; 210/729; 210/735; 210/764; 252/180; 252/344; 252/358; 558/232; 558/233; 558/235; 558/236; 558/237
[58] Field of Search .................. 544/357, 389, 401; 558/235, 236, 237, 232, 233; 210/764, 708, 729, 735; 252/358, 344, 180

[56] References Cited

U.S. PATENT DOCUMENTS

| | | | |
|---|---|---|---|
| 1,788,632 | 1/1931 | Powers | 558/236 |
| 2,457,209 | 12/1948 | Clark | 260/72 |
| 2,589,209 | 3/1952 | Kardos | 260/72 |
| 3,753,931 | 8/1973 | Raspanti | 260/2 BP |
| 3,876,550 | 4/1975 | Holubec | 252/47.5 |
| 4,689,177 | 8/1987 | Thompson et al. | 252/344 |
| 4,826,625 | 5/1989 | Thompson et al. | 252/344 |
| 4,855,060 | 8/1989 | Durham et al. | 210/708 |
| 4,864,075 | 9/1989 | Thompson et al. | 558/237 |
| 4,956,099 | 9/1990 | Thompson et al. | 210/764 |
| 5,006,274 | 4/1991 | Durham et al. | 252/180 |
| 5,013,451 | 5/1991 | Thompson et al. | 210/708 |
| 5,019,274 | 5/1991 | Thompson et al. | 210/729 |
| 5,026,483 | 6/1991 | Thompson et al. | 210/708 |

FOREIGN PATENT DOCUMENTS

| | | |
|---|---|---|
| 771181 | 11/1967 | Canada. |
| 0013462 | 5/1983 | European Pat. Off.. |
| 0249320 | 12/1987 | European Pat. Off.. |
| 0200143 | 8/1990 | European Pat. Off.. |
| 8910956 | 11/1989 | World Int. Prop. O.. |

OTHER PUBLICATIONS

A. M. Gaudin, Flotation, McGraw-Hill, New York, 1957, pp. 182-183 and 209-211.
T. Kitson, "The Dithiocarbamates—Interesting, Versatile and Neglected", Education in Chemistry, Mar. 1985, pp. 43-45.
Chemical Abstracts 104(86):23816a (1986).
S. Gutcho, Waste Treatment with Polyelectrolytes and Other Flocculants, Noyes Data, Park Ridge, N.J., 1977, pp. 81-82 and 96-98.
Chemical Abstracts 112(90):41931d (1990).
F. J. Kenney, "Use of Surfactants in Mineral Flotation", Industrial Applications of Surfactants, D. R. Karsa, Ed., Royal Society of Chemisty, Cambridge, England, 1990, pp. 369-370.

Primary Examiner—Cecilia Tsang
Attorney, Agent, or Firm—Rosenblatt & Associates

[57] ABSTRACT

Dithiocarbamic salts made from the reaction products of certain polyamines and epoxides have been found to be useful to clarify water, particularly the oil-in-water emulsions which accompany crude oil production. The water clarification may be accomplished by demulsification or flocculation. The polyamine reaction products themselves are novel and may have the structure

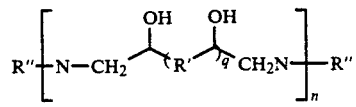

where R" is selected from the group consisting of the structure —R—NH$_2$ and

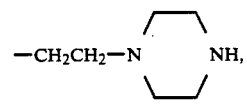

where R is selected from the group consisting of straight, branched or cyclic alkylene moieties; arylene moieties; substituted straight, branched or cyclic alkylene moieties; substituted arylene moieties or mixtures thereof; and where R' is $$-(CH_2)_m-O-R-O-(CH_2)_m-$$

where n and m independently range from 1 to 5 and q is 0 or 1. The dithiocarbamic salts made from these polyamines also find use as corrosion inhibitors.

22 Claims, No Drawings

EPOXY MODIFIED WATER CLARIFIERS

FIELD OF THE INVENTION

The invention relates to novel polyamines and dithiocarbamic salts made therefrom, and more particularly the invention relates, in one aspect, to polyamines and dithiocarbamic salts therefrom which have exhibited water clarifying capabilities for oil field emulsions.

BACKGROUND OF THE INVENTION

Any refinery process water, petroleum chemical waste water, ballast waste water, river water, underground feed water, ethylene quench waste water, oil-in-water waste emulsions from oil recovery fields, and the like are contaminated waters requiring difficult chemical treatment and clarification. These aqueous systems are also found in steam cylinder dispersions in which small amounts of oils which are used for lubrication may be found in the steam of engines and pumps; emulsions and other dispersions containing polystyrene and styrenes-in-water frequently found in synthetic rubber manufacturing facilities; emulsions and other dispersions obtained during clay pipe manufacture using steam initiated processes; oil-in-water emulsions or dispersions which are found in coolant water devices and in gasoline absorption facilities; emulsions and dispersions containing wax-type products which are encountered in oil refinery dewaxing procedures; "fluxoil" emulsions and dispersions occurring in condensate steam resulting in dehydrogenation of butylene during catalytic procedures to produce butadiene; emulsions and dispersions obtained during procedures for making butadiene from naphtha by means of standard "cracking" procedures in gas generators; emulsions and dispersions in latex-in-water formed in copolymerization procedures for butadiene and styrene derivatives.

Such dispersions and emulsions are also problems in synthetic resin paint and pigment manufacturing processes, as well as in food processing of derivatives of pasteurized additives. In each of these processes, as well as in the equipment which is used during steps in the various procedures, oil-in-water emulsions or dispersions of a non-aqueous phase are inherently formed as a by-product of the particular given operation. The disposal of the produced waste water becomes a problem which is compounded by the presence of the oil-in-water emulsions, or dispersions containing a non-aqueous discontinuous phase. Often, extreme difficulties are presented in the treatment and clarification processes employed. If one were to successfully treat these kinds of waste waters which contain oily waste matter as well as dispersed solid matter of an organic or inorganic nature, one could advance the art of treating and clarifying contaminated waters of this type.

The present invention is directed to the clarification of such aqueous systems, so that the resultant stream of the aqueous system contains essentially two separate phases; an oil- or hydrocarbon-based phase, or non-aqueous phase, and an essentially aqueous phase, with the resultant aqueous phase being clarified without the production of a problematic floc. Clarification is accomplished with water clarifiers which are compounds which, when added to produced water containing oil, form "flocs." The dispersed oil and solid particulates absorb on the floc and thereby are removed from the water when the floc is skimmed off the surface of the treated water. The treated aqueous system can then pass certain industrial and/or governmental water clarity tests or specifications and be discharged. The dispersed oil and/or solid particulates may also be recovered.

The aqueous systems contemplated in this invention will contain water in various forms, such as tap water, brines or seawater (in the case of aqueous systems involved in the drilling, completion, workover or production of subterranean oil or gas wells), and the like.

In any oil-in-water emulsion, the amount of oil in the water or aqueous phase, or in the case of a dispersion of non-aqueous phase, the amount of such non-dispersed phase will vary considerably depending on the industrial application. In the case of emulsions which are frequently found in the oil field and in applications of well completion operations, the oil-in-water emulsion will contain a crude oil content varying from a few parts per million to about 20%, by volume or even higher.

In treating such emulsified or dispersed aqueous systems for disposal or other uses or recycling, it is necessary to break the emulsified oil-in-water or resolve the dispersion such that the oil phase, or the non-aqueous dispersed phase and the water phase may be separated. The water should be clarified by the demulsification treatment without production of a problematic "floc".

"Floc" is considered to be a by-product of water clarification which may vary in characteristics depending on the composition of the clarifier used to clarify the water. While "floc" may always be expected to be produced as a result of a water clarification treatment procedure, such "floc" should be made to be controllable. A problematic floc may adversely affect operations or clarification systems by means of adherence, plugging and interface problems with manufacturing equipment or production equipment. Floc characteristics can be visually judged by observing a sample of the treated aqueous system. The present invention contemplates water clarification such that the floc which is formed does not cause operational problems in the treatment system by means of adherence, plugging, or interface buildup with equipment being exposed to the aqueous system. An improved floc is one that is easily skimmed and does not build up in the system—essentially, a floc which is easier to handle.

In the past, those skilled in the art have recognized the use of derivatives of certain amines as demulsifiers in water clarification procedures. These derivatives are obtained by reacting amines with carbon disulfide and materials which are sources of alkali metal ions, alkali earth metal ions, ammonium ions and amine ions from other reactants. The preparation of dithiocarbamates has long been known, see for example, U.S. Pat. No. 1,788,632 which describes a process of making these organic sulfur compounds. U.S. Pat. No. 2,457,209 teaches dithiocarbamates as resinous adhesives. Lubricant compositions comprising an additive combination to improve the anti-oxidant and rust-inhibiting properties of these compositions are disclosed in U.S. Pat. No. 3,876,550. European Patent 13,462 B1 describes compositions comprising mixtures of a dithiocarbamic acid derivative and a sulfonium compound such as triphenylsulfonium chloride and suggest they provide effective corrosion inhibition in acid treatment of metal in the presence of a copper complexing agent such as thiourea.

Dithiocarbamates have also been known to be used as separation agents. For example, see U.S. Pat. No. 2,589,209 which mentions that dithiocarbamate-aldehyde condensation polymers may be useful as flotation agents. Typical of such prior art are U.S. Pat. Nos. 4,689,177; 4,826,625; 4,864,075; 4,956,099 and 5,013,451, which teach the use of nitrogen-containing dithiocarbamic acid compositions formed by the reaction of alkoxylated triamines with $CS_2$ as "reverse" demulsifiers. While certain of the materials disclosed in these patents may or may not be used satisfactorily to demulsify particular aqueous systems, it has been found that not all such materials are satisfactory to clarify water without the production of a resultant problematic floc. U.S. Pat. Nos. 5,013,451 and 5,019,274 teach a different set of dithiocarbamates for water clarification by demulsification and flocculation, respectively, from those mentioned in the '177; '625 and '075 patents. The dithiocarbamates of the '451 and '274 patents are made using non-alkoxylated and alkoxylated amines having linear, branched and cyclic aliphatic carbon chains.

European Patent Application 249,320 describes dithiocarbamates made from alkyl and alkenyl diamines, alkyl and alkenyl triamines and alkyl and alkenyl tetramines. The application states that these compositions are useful as ferrous iron sequestrants in acidic solutions containing high percentages of acid, and with methods of use thereof as aids in reducing asphaltene precipitation in asphaltenic reservoirs treated with a solution of strong acid.

U.S. Pat. Nos. 4,855,060 and 5,006,274 notes that if bis(hexamethylene)triamine (BHMT) is reacted in an approximate stoichiometric ratio of primary amine with carbon disulfide, that the resultant product can be used to successfully break the emulsion and clarify the water, without the production of a problematic floc. In U.S. Pat. Nos. 4,855,060 and 5,006,274, these problematic flocs were termed "uncontrollable" and it will be understood that these terms refer to the same kinds of undesirable flocs. The commercial product related to the material of this patent is marketed by Baker Performance chemicals, Inc. as MAGNACLEAR® W213 water clarifier, referred to herein as W213. MAGNACLEAR® W213 is a trademark for water clarifier products made by Baker Performance Chemicals, Inc.

International application WO 89/10956 describes quaternary ammonium dithiocarbamate compounds and methods of preparing the same by mixing in water a quaternary ammonium compound and a dithiocarbamate salt or a bis-dithiocarbamate salt and recovering the quaternary ammonium dithiocarbamate compound from the organic layer formed thereby. The compositions employing such compounds are said to be primarily useful as surfactants and biocides and also in water treatment in oil drilling or recovery operations, in fuel, cutting fluids and in the flotation of heavy metal ores in mineral beneficiation. Dithiocarbamates made from bis-hexamethylenetriamine were found to be useful as ore flotation agents in Canadian Patent 771,181.

Indeed, dithiocarbamates have been known as ore flotation agents for some time; see, for example, A. M. Gaudin, *Flotation*, McGraw-Hill, New York, 1957, pp. 182-183 and 209-211. The separation of heavy metal ions from aqueous solutions using dithiocarbamates is also recognized by T. Kitson in "The Dithiocarbamates —Interesting, Versatile and Neglected,", *Education in Chemistry*, March, 1985, pp. 43-45. A di-methyl dithiocarbamate is taught together with other compounds to assist in solid-liquid separation of copper plating wastewater according to *Chemical Abstracts* 104(86):23816a. Similarly, the treatment of wastewater containing heavy metal complexes, such as those of copper, iron, zinc or nickel, may be accomplished using dithiocarbamate or other materials as described in *Chemical Abstracts* 112(90):41931d. Dithiocarbamates are listed as collectors in ore flotation by F. J. Kenney in an article "Use of Surfactants in Mineral Flotation" which appeared in *Industrial Applications of Surfactants*, D. R. Karsa, Ed., Royal Society of Chemistry, Cambridge, England, 1990, p. 369-370.

Epoxy modified materials have also found uses in separation procedures. For example, U.S. Pat. No. 3,753,931 is directed to water soluble, high molecular polyetheramines and their salts, produced by the reaction, in excess, of aliphatic polyamines which contain at least one primary or two secondary amino groups, may contain hydroxyl groups and have molecular weights not greater than 200, with polyepihalogeno-hydrins which contain 3 to 25 halogenomethyl groups. Removal of excess polyamine from the reaction mixture by distillation follows next, reaction of the resulting polyether amine aqueous solution with crosslinking agents to a degree of crosslinking at which a viscosity increase occurs and the reaction mixture remains water soluble, and if desired partial or complete conversion of the free amino groups into their salts by the addition of acids. These polyamines are useful as flocculating and flotation agents and as drainage and retention aids, especially in paper manufacture.

Other such patents are discussed by S. Gutcho in Waste Treatment with Polyelectrolytes and Other Flocculants, Noyes Data, Park Ridge, N.J. 1977, pp. 81-82 (U.S. Pat. No. 3,493,502—"Condensation Product of Methylamine with Epichlorohydrin for Settling of Ore and Mineral Solids"), pp. 96-98 (U.S. Pat. No. 3,741,891—"Ilmenite Digestion Liquor Treated by an Alkyl Quaternary Epihalohydrin-Monoalkylamine Product"). Similarly, a metal scavenger comprising an addition product of a polyamine and an epihalohydrin is described in European Patent 200,143 B1, the addition product containing as a substituent at least one carbodithio group and/or at least one carbodithioate salt group introduced therein by substituting the corresponding number of active hydrogen atoms in the addition product.

On an oil and gas production site, dithiocarbamic salt water clarifiers work in conjunction with gravity settling equipment, flotation devices, filtration equipment and the like by creating a floc with metal ions in the brine. After the oil and grease have absorbed onto the surface of the floc, the floc is separated and returned to crude production. Most prior flocs are "sticky" and adhere to surfaces inside the equipment. After a relatively short period of time, the build-up of floc on the skimmer, walls and in the trough causes the unit to need to be shut down and cleaned. Preferably, the water clarifier provides an "acceptable" floc which does not cause operational problems in the system via adherence, plugging and interface build-up.

SUMMARY OF THE INVENTION

Accordingly, it is an object of the present invention to provide unique polyamines which, when derivatized with carbon disulfide ($CS_2$) to make the dithiocarbamic salts, have water clarifying properties when used in conjunction with oil-in-water emulsions resulting from crude oil production.

It is another object of the present invention to provide new polyamines and dithiocarbamic salts made therefrom using commercially available materials, such as amines and polyepoxides.

Another object of the present invention is to provide a new class of dithiocarbamic salts which have utility as water clarifiers for oil field emulsions with the production of little or no problematic floc.

In carrying out these and other objects of the invention, there is provided, in one form, polyamine compounds of the formula:

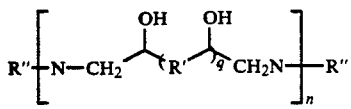

—where R" is selected from the group consisting of the structure—R—NH$_2$ and

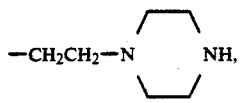

wherein R is selected from the group consisting of straight, branched or cyclic alkylene moieties; arylene moieties; substituted straight, branched or cyclic alkylene moieties; substituted arylene moieties or mixtures thereof; and where R' is

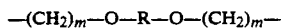

where n and m independently range from 1 to 5 and q is 0 or 1.

DETAILED DESCRIPTION OF THE INVENTION

It has been discovered that commercially available amines may be modified with polyepoxide materials to produce novel polyamines, which, in turn, may be reacted with carbon disulfide (CS$_2$) and a source of alkali metal ion, alkali earth metal ion, ammonium ion or amine ion to product dithiocarbamic salts which have water clarifying properties when used to demulsify or flocculate oil-in-water emulsions, particularly those found in oil field production.

Generally, the polyamines of this invention may be produced according to the following general equation:

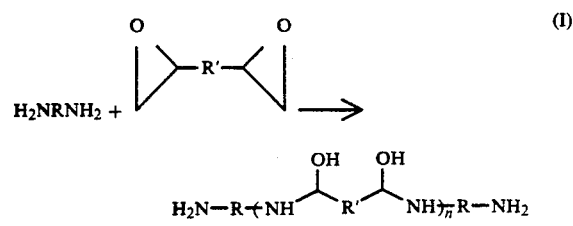

where R is selected from the group consisting of straight, branched or cyclic alkylene moieties, arylene moieties, substituted straight, branched or cyclic alkylene moieties, substituted arylene moieties or mixtures thereof; and where R' is

where n and m are independently 1 to 5.

In another embodiment of the invention, the polyamine compounds of the invention may have the formula:

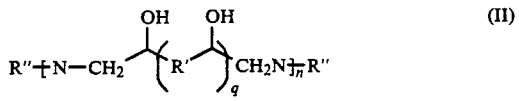

wherein R" is selected from the group consisting of the structure—R—NH$_2$ and

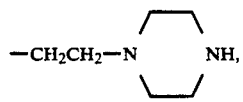

where R is selected from the group consisting of straight, branched or cyclic alkylene moieties; arylene moieties; substituted straight, branched or cyclic alkylene moieties; substituted arylene moieties or mixtures thereof; and where R' is

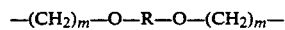

where n and m independently range from 1 to 5 and q is 0 or 1. In one embodiment of the invention, n and m independently range from 1 to 2.

The novel polyamines (II) may be further reacted with CS$_2$ and a source of an alkali metal ion, an alkaline earth metal ion, ammonium ion or an amine ion to give a dithiocarbamic salts of the formula:

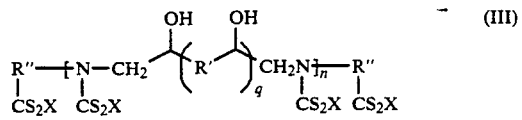

where X is hydrogen, an alkali metal, an alkaline earth metal, ammonium ion or an amine, and the other terms are as defined above. For example, if potassium hydroxide (KOH) is the alkali metal ion source, then potassium (K) is X in dithiocarbamate compound (III).

Specific examples for R include, but are not limited to moieties such as the following:

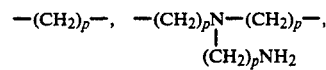

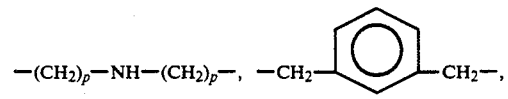

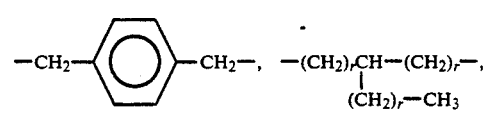

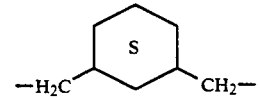

where

is a saturated (e.g. cyclohexane) moiety and where p is from 1 to 8, r is 0 to 8, and mixtures thereof. In one embodiment, the polyamine coreactants have from 2 to 30 carbon atoms. The coreactants should have at least two primary amine groups, but more than two are permitted. It is expected that compounds having an average of about 3 or more secondary amine groups would be suitable for this invention, and possible compounds with only two secondary amine groups. Representative materials for these polyamine coreactants include, but are not limited to ethylene diamine, the tris-(2-aminoethyl)amine product TREN ® sold by W. R. Grace & Co., having the structure $N(CH_2CH_2NH_2)_3$; the diamine Dytek ® sold by E. I. DuPont de Nemours, Co., having the structure $H_2NCH_2CH(CH_3)CH_2CH_2CH_2NH_2$; hexamethylenediamine; metaxylylidenediamine; aminoethylpiperazine sold by Texaco Chemical Co. and Union Carbide Corp. and the like. Specific examples for R' include, but are not limited to alkoxy groups, such as ethoxy, propoxy, butoxy and the like and mixtures thereof, e.g. $—CH_2OCH_2CH_2OCH_2—$ as well as a bisphenol A diether moiety such as:

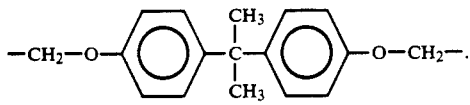

The polyepoxide coreactants may be diepoxides, haloepoxides and dihalo organic compounds having the formula Y—R″—Y where R″ is the organic moiety and Y is Cl, Br, I, or $O_3SR''$. Specific examples of suitable polyepoxide materials include, but are not limited to, Epon 828 ® and Epon 1031 resins sold by Shell Chemical Company; ethylene glycol diglycidyl ether and epihalohydrins, as mentioned; NC-514 and NC-551 resins sold by Cardolite Corporation.

It is within the scope of this invention that monoepoxide compounds may also serve as crosslinkers for the polyamine reactants mentioned above. Suitable monoepoxides include, but are not limited to, epihalohydrins such as epichlorohydrin to give materials according to the following reaction scheme:

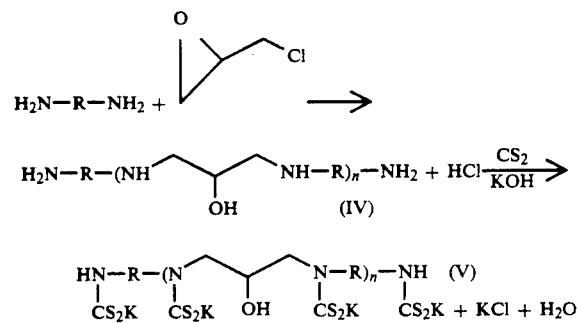

where R and n are as above.

The molar ratio of polyamine reactant to mono- or polyepoxide may be in the range from 1:1 to 1000:1, in one embodiment from 1:1 to 100:1, and preferably from about 1.5:1 to 2.5:1, most preferably 2.0:1.

As used herein, the term "aqueous system" is intended to mean and refer to any water-based stream, the major constituent of which is either tap water, fresh water, a brine, salt water, seawater, or the like, either as a natural additive during a commercial manufacturing procedure, or in the fluids which are used to drill, complete, or workover a subterranean oil or gas well, in production streams of fluid hydrocarbons from subterranean wells, and the like. Also as used herein, the oil or other dispersed constituent in the oil-in-water emulsion or dispersion of a non-aqueous discontinuous phase which occurs in such aqueous systems may either be produced hydrocarbons, such as those which are found in a production well, or any hydrocarbon- or grease-containing chemicals, sulfur or similar constituent found in many typical manufacturing procedures, such as those described above.

The process of the present invention contemplates contacting the aqueous system containing the oil-in-water emulsion or dispersion of the non-aqueous discontinuous phase with an effective amount of the composition of the invention. Such contact can occur in a variety of forms, such as by introduction of a "pill" or "slug" of composition through a treatment line or conduit, as known to those skilled in the art in the treatment of produced hydrocarbons from subterranean oil and gas wells, or by a continuous injection procedure. Additionally, the composition may be added to the aqueous system prior to formation of the oil-in-water emulsion or dispersion, or may be added to the water phase which is subsequently found to contain the oil-in-water emulsion or dispersion. Typically, however, the invention will be utilized in an injection procedure wherein the composition will be continuously, or incrementally, introduced into the aqueous system containing the oil-in-water emulsion or dispersion of a non-aqueous discontinuous phase.

The invention contemplates introduction of the composition at any desired point during the treatment of the aqueous system, such as prior to or at gravity settling equipment, flotation devices, filtration processes, sales lines, and the like. Because of obvious variations in operating parameters, such as type and quantity of oil or other hydrocarbon or other constituents comprising the dispersed non-aqueous discontinuous phase, the amount and quantity of water in the system, the clarification required for the treated aqueous system, and other physical and chemical parameters, as well as the particular dithiocarbamic salt selected for use, an exact level of required additive cannot be specified. Those skilled in the art will recognize tat known clarification and floc evaluation tests, such as those specifically disclosed herein, may easily be used to determine the appropriate level of treatment for the particular application at hand.

The present invention contemplates maintaining the water clarifier composition with the dithiocarbamic salt in the aqueous system for sufficient time to effectively clarify the system and to control the resultant floc which occurs as a result of the clarification procedure. Of course, the water quantity and quality, the tightness and content of the oil-in-water emulsion or the dispersion of the non-aqueous discontinuous phase and other chemical and physical variables will dictate the amount of time which is required to effectively clarify the water for the particular end use applications or disposal technique at hand. Those skilled in the art may utilize simple water clarification and floc tests, such as those described below, to determine, among other things, the amount of time required to maintain the composition in the system for effective water clarification.

In determining the ability of a composition, including the additive of the present invention, to clarify an aqueous system and produce a controllable resultant floc, the aqueous system with the composition added thereto is simulated. Water quality is then determined using gravimetric, spectrophotometric, or visual means.

The invention will be illustrated more completely by the following Examples, which are not intended to limit the invention, but are simply instructive thereto.

EXAMPLE 1

Production Procedure for RE 1891

The following components are listed in their order of addition.

| Material | MW | Grams | Equiv. | Wt. % | % Solids |
|---|---|---|---|---|---|
| Ethylene diamine (EDA) | 60 | 13.06 | 2 | 7.47 | 7.47 |
| Propylene glycol (PG) | — | 41.53 | — | 23.74 | — |
| Epon ® 828 | 342 | 37.24 | 1 | 21.29 | 21.29 |
| Purge loss | 60 | (3.27) | (0.5) | (1.87) | (1.87) |
| Water | — | 20.77 | — | 11.88 | — |
| 45% Aqueous KOH | 124.7 | 40.73 | 3 | 23.29 | 7.12 |
| Carbon disulfide ($CS_2$) | 76 | 24.83 | 3 | 14.20 | 14.20 |
| | | | | 100 | 48.21 |

Epon 828 was weighed into a solution of EDA in PG. The mixture was then stirred at room temperature. The reaction exothermed to about 70° C. The mixture was then stirred overnight at room temperature. It might be possible to reduce this period to 2-3 hours by heating the solution at 65°-70° C. after the exotherm breaks. Vacuum at 22-26" was put on the reaction, and a heat lamp was used to keep the walls o the flask warm. The temperature was then brought up to 65° C. The temperature was raised to about 100° C. over about one hour. The solution was then stirred at 100° C. under a vacuum for four hours.

With vigorous stirring, at about 65° C., water was added dropwise to the solution. Then the KOH solution was added dropwise. A white suspension formed. It is noted that slow addition of water and caustic tends to form a fine suspension. Adding these components in one slug tends to form a rubbery mass. The mixture was cooled to room temperature and $CS_2$ was added at a rate to keep the temperature below about 40° C. The white suspension became an orange-red solution.

EXAMPLE 2

Use as Water Clarifier

The dithiocarbamic salt product of Example 1 was used at a level of 40 ppm in bottle tests at an offshore oil platform in the Gulf of Mexico and produced bright and clear water; as contrasted with 100 ppm of the product of U.S. Pat. No. 4,855,060 which did not clarify the water.

The bottle test is a method in which samples of a selected fluid are treated with varying levels of chemicals to be evaluated and agitated in a manner simulating conditions in a given aqueous system. After settling for a designated period, the performance of the chemicals is observed. These tests are quite qualitative.

In evaluating compositions for their ability to clarify a given aqueous system, care should be exercised to ensure that the sample used for testing is representative of the aqueous system to be treated. The sample point should be selected at a location where the fluid is preferably a composite of the fluids being treated in the system and is at a point in close proximity to where the chemical is likely to be applied. Preferably, a sample tap should be located at the bottom of a pipe or conduit to allow sampling of the water external phase. In obtaining the sample, the sample valve should be open to an extent to minimize shearing of the emulsion or interference with the dispersion of the non-aqueous discontinuous phase. Before any testing is carried out, the emulsion or dispersion to be tested should be verified as having an aqueous continuous phase in a known manner. Using a syringe, samples of the aqueous system are injected with varying treatment levels of the treatment composition. The sample containers are capped and agitated by either hand shaking or use of a mechanical oscillating shaker. After agitation, the fluids are allowed to settle for a duration and under conditions which have been determined to correlate with the system conditions. At the end of the settling period, evaluations of the performance of each sampled material are made by visual appearance, using the following criteria:

E=Excellent: Water is cleaned with distinct sparkle and no visible suspended particles.

G=Good: Water has light haze (white) and/or carries light amounts of suspended material.

F=Fair: Water has distinct coloration, either as a haze or from the presence of suspended particles.

P=Poor: Treatment has had an effect, but water remains very turbid and/or colored.

B=Bad: No effective treatment, equal to untreated sample.

Intermediate Rating: (+)=better than; (−)=poorer than.

The given sample of the aqueous system containing the treating composition is tested, as above, and thereafter, oil and grease are separated from the water (if any such oil and grease is apparent) by known chemical means, and the concentration of such material determined. Of course, the less oil and grease in the sample, the more satisfactory water clarification. In the working examples and in the claims, water clarifying performance is expressed as residual concentration of oil and grease.

In determining the ability of a composition, including the dithiocarbamate additive of the present invention, to clarify an aqueous system and produce a controllable resultant floc, the aqueous system with the composition added thereto is simulated. Water quality is then determined using gravimetric, spectrophotometric, or visual means. A floc rating is then established using techniques described below.

In the examples below, the formation of an acceptable or unacceptable floc was determined by bench scale flotation procedures. If the floc was deemed by visual appearance to be problematic, a floc rating of "U" was given. On the other hand, a floc which was deemed to be acceptable and controllable was given a floc rating of "A".

The presence of a problematic floc is easily determinable by visual observation during bench testing procedures. During such tests, any floc which appears is visually rated against an "acceptable" and known control sample which has been treated with a material to clarify the water without production of a problematic floc. The following rankings are then applied to the particular sample:

Acceptable: Loose, brown appearance.
Acceptable: Agglomerated, brown, appearance.
Unacceptable: Loose, black, powdery, appearance.
Unacceptable: Agglomerated, black, powdery, appearance.
Unacceptable: Agglomerated, black, ropy appearance; adheres to solid surfaces.
Unacceptable: Agglomerated, black, plastic appearance; adheres to solid surfaces.

As noted previously, an acceptable floc does not cause operational problems in the system by adherence, plugging, and interface build-up. An unacceptable floc formation causes operational problems in the system by means of adherence, plugging and interface problems. This testing procedure is referred to as the Floc Manageability Determination Method.

In the working examples, set forth in Table I, various water clarifying compositions were evaluated by both bottle and bench scale flotation testing procedure.

TABLE I

Flocculation and Bench Scale Flotation Results

| Ex. | Product | Activity Approx. % | Description | Water Quality Bottle Test Data | | | | Bench Scale Flotation Cell | | |
|---|---|---|---|---|---|---|---|---|---|---|
| | | | | ppm | Initial | Final | Floc | ppm | ppm Oil | Floc |
| A | RE 1857 | 25 | Diallylamine methacrylic copolymer/CS$_2$ | 100 | P | P+ | A | 30 | 20 | A |
| B | RE 1857 | 25 | Diallylamine methacrylic copolymer/CS$_2$ | 200 | F | F+ | A | 60 | 16 | A |
| C | RE 1857 | 25 | Diallylamine methacrylic copolymer/CS$_2$ | 400 | F+ | G− | A | | | |
| D | RE 1891[1] | 25 | Epon 828/EDA/CS$_2$ | 100 | P | P+ | A | 30 | 13 | A |
| E | RE 1891 | 25 | Epon 828/EDA/CS$_2$ | 200 | F+ | F+ | A | 60 | 9 | A |
| F | RE 1891 | 25 | Epon 828/EDA/CS$_2$ | 400 | G | G | A | | | |
| G | RE 1863 | 25 | Epon 828/TREN/CS$_2$ | 100 | P | P+ | A | 30 | 19 | A |
| H | RE 1863 | 25 | Epon 828/TREN/CS$_2$ | 200 | F | F+ | A | 60 | 15 | A |

[1]Material of Example 1.

TABLE II

Identification of Inventive Compounds

The dithiocarbamate compounds of this invention may be defined according to the following formula:

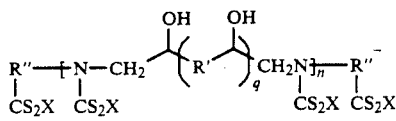

where R" is selected from the group consisting of the structure —R—NH$_2$ and

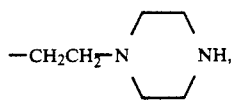

where R is selected from the group consisting of straight, branched or cyclic alkylene moieties; arylene moieties; substituted straight, branched or cyclic alkylene moieties; substituted arylene moieties or mixtures thereof; and where R' is —(CH$_2$)$_m$—O—R—O—(CH$_2$)$_m$— where n and m independently range from 1 to 5 and q is 0 or 1; and where X is hydrogen, an alkali metal, an alkaline earth metal, ammonium ion or an amine.

| Compound | R | R' | R" | m n q |
|---|---|---|---|---|
| 1103-189-2 | — | —CH$_2$—O—⟨C$_6$H$_4$⟩—C(CH$_3$)$_2$—⟨C$_6$H$_4$⟩—O—CH$_2$— | —CH$_2$CH$_2$—N(piperazine)NH | 1 1 1 |
| 1103-193-2 | —(CH$_2$)$_6$NH(CH$_2$)$_6$— | " | —R—NH$_2$ | 1 1 1 |
| 1103-183-2 | —(CH$_2$)$_2$NH(CH$_2$)$_2$— | " | —R—NH$_2$ | 1 1 1 |
| RE 1857 | Copolymer of methacrylic acid (CO$_2$H) and diallylamine (NH) | | | |
| RE 1863 | —CH$_2$CH$_2$N(CH$_2$CH$_2$NH$_2$)—CH$_2$CH$_2$— | —CH$_2$—O—⟨C$_6$H$_4$⟩—C(CH$_3$)$_2$—⟨C$_6$H$_4$⟩—O—CH$_2$— | —R—NH$_2$ | 1 1 1 |

TABLE II-continued

Identification of Inventive Compounds

| | | | | |
|---|---|---|---|---|
| RE 1864 | —(CH$_2$)$_6$— | " | —R—NH$_2$ | 1 1 1 |
| RE 1932 | —(CH$_2$)$_2$— | " | " | 1 1 1 |
| RE 1989 | –C$_6$H$_4$– (para-phenylene) | — | " | 1 1 0 |
| RE 1991 | —CH$_2$–C$_6$H$_4$–CH$_2$— | —CH$_2$—O—CH$_2$CH$_2$—O—CH$_2$— | " | 1 1 1 |
| RE 1992 | —CH$_2$–C$_6$H$_4$–CH$_2$— | — | " | 1 1 0 |
| RE 1993 | " | —CH$_2$—O—CH$_2$CH$_2$—O—CH$_2$— | " | 1 1 1 |
| RE 1994 | " | —CH$_2$—O—C$_6$H$_4$—C(CH$_3$)$_2$—C$_6$H$_4$—O—CH$_2$— | " | 1 1 1 |
| RE 1996 | cyclohexylene | —CH$_2$—O—CH$_2$CH$_2$—O—CH$_2$— | " | 1 1 1 |
| RE 1997 | cyclohexylene | — | " | 1 1 0 |
| RE 1998 | " | —CH$_2$—O—CH$_2$CH$_2$—O—CH$_2$— | " | 1 1 1 |
| RE 1999 | " | —CH$_2$—O—C$_6$H$_4$—C(CH$_3$)$_2$—C$_6$H$_4$—O—CH$_2$— | " | 1 1 1 |
| RE 2000 | —CH$_2$CH$_2$CH$_2$CH(CH$_3$)CH$_2$— | — | " | 1 1 0 |
| RE 2001 | " | —CH$_2$—O—CH$_2$CH$_2$—O—CH$_2$— | " | 1 1 1 |
| RE 2002 | " | —CH$_2$—O—C$_6$H$_4$—C(CH$_3$)$_2$—C$_6$H$_4$—O—CH$_2$— | " | 1 1 1 |
| RE 2003 | —CH$_2$CH$_2$CH(CH$_2$CH$_3$)— | — | " | 1 1 0 |
| RE 2004 | " | —CH$_2$—O—CH$_2$CH$_2$—O—CH$_2$— | " | 1 1 1 |
| RE 2005 | " | —CH$_2$—O—C$_6$H$_4$—C(CH$_3$)$_2$—C$_6$H$_4$—O—CH$_2$— | " | 1 1 1 |

TABLE II-continued
Identification of Inventive Compounds

RE 2012 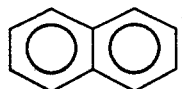 O—CH₂CHCH₂—NH—(CH₂)₃NH(CH₂)₃NH₂
                               |
                               OH RE 2013 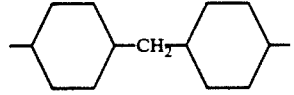  —  " 1 1 0

20% trans, trans isomer

RE 2014 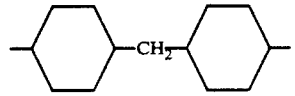 —CH₂—O—CH₂CH₂—O—CH₂— " 1 1 0

20% trans, trans isomer

RE 2015 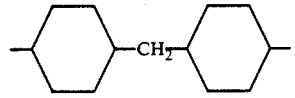 — " 1 1 1

48% trans, trans isomer

RE 2016 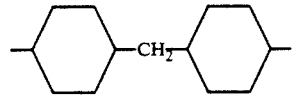 —CH₂—O—CH₂CH₂—O—CH₂— " 1 1 1

48% trans, trans isomer

TABLE III

Examples 3-31

Dithiocarbamic Salts as Water Clarifiers

The materials identified above in Table II were tested in bottle tests using water samples obtained from platforms in the Gulf of Mexico, according to the bottle test procedures described above.

The following compounds were found to be "above average", i.e. providing bright, clear water as a dose of about 10-20 ppm. RE 1932 was found to produce a very manageable floc.

| Ex. | Compound |
|---|---|
| 3 | RE 1932 |
| 4 | 1103-189-2 |
| 5 | 1103-193-2 |
| 6 | 1103-183-2 |
| 7 | RE 1991 |
| 8 | RE 1993 |
| 9 | RE 1999 |
| 10 | RE 2000 |
| 11 | RE 2001 |
| 12 | RE 2004 |
| 13 | RE 2012 |
| 14 | RE 2014 |
| 15 | RE 2016 |
| 16 | RE 1857 |
| 17 | RE 1862 |
| 18 | RE 1863 |
| 19 | RE 1864 |

The following compounds were found to be "average", i.e. providing water not as clear as those above at a dose of about 10-20 ppm.

| Ex. | Compound |
|---|---|
| 20 | RE 1992 |
| 21 | RE 1989 |
| 22 | RE 1994 |
| 23 | RE 1996 |
| 24 | RE 1997 |
| 25 | RE 1998 |
| 26 | RE 2002 |
| 27 | RE 2003 |
| 28 | RE 2004 |
| 29 | RE 2005 |
| 30 | RE 2013 |
| 31 | RE 2015 |

EXAMPLES 32-41

Dithiocarbamates as Corrosion Inhibitors

Various of the dithiocarbamates of this invention were tested as corrosion inhibitors. The test conditions involved solutions of 5% NaCl brine in a $CO_2$ atmosphere at a temperature of 20°-25° C. Often 10% kerosene was employed as an oil phase. The corrosion rates in mpy (mils per year—one thousandths inches of metal lost per year) were measured electrochemically at approximately 1 hour intervals. The amount of dithiocarbamic salt in each Example was 100 ppm. The results are reported in Table IV.

TABLE IV

Examples 32-41; Dithiocarbamic Salts as Corrosion Inhibitors

| Time, hr. | Corr. rate, mpy | Comments |
|---|---|---|
| Ex. 32 | RE 1862 | ($CO_2$/brine/kerosene) |
| 0 | 60 | No foam |
| 1 | 1.5 | No emulsion |
| 2 | 1.5 | Black floc and deposits |
| 3 | 1.5 | |
| Ex. 33 | RE 1862 | ($CO_2$/brine) no oil phase |
| 0 | 60-70 | |
| 1 | 0.9 | |
| 2 | 0.7 | |
| 3 | 0.5 | |
| Ex. 34 | 1103-191-2 | ($CO_2$/brine/kerosene) |
| 0 | 60 | Brownish color |
| 1 | 0.4 | No foam |
| 2 | 0.3 | No emulsion |
| 3 | 0.2 | Oil phase very clean |
| Ex. 35 | 1103-189-2 | ($CO_2$/brine/kerosene) |
| 0 | 70 | |
| 1 | 1.75 | No foam |
| 2 | 0.5 | No emulsion |
| 3 | 0.3 | No black deposits/solids |
| Ex. 36 | RE 2000 | ($CO_2$/brine/kerosene) |
| 0 | 60 | No foam |
| 1 | 1.5 | No floc |
| 2 | 0.4 | No emulsion |
| 3 | 0.3 | |
| Ex. 37 | 1103-191-2 | ($CO_2$/brine/kerosene) |
| 0 | 60 | |
| 1 | 0.35 | No emulsion |
| 2 | 0.25 | No foam |
| 3 | 0.20 | Very clean oil |
| Ex. 38 | RE 2000 | ($CO_2$/brine/kerosene) |
| 0 | 70 | |
| 1 | 0.60 | Heavy floc |
| 2 | 0.40 | No emulsion |
| 3 | 0.35 | |
| Ex. 39 | 1193-189-2 | ($CO_2$/brine/kerosene) |
| 0 | 70 | No emulsion |
| 1 | 0.45 | No foam |
| 2 | 0.35 | No black deposits or solids |
| Ex. 40 | RE 2000 | ($CO_2$/brine/kerosene) |
| 0 | 70 | |
| 1 | 0.35 | Heavy floc |
| Ex. 41 | RE 1879 | ($CO_2$/brine/kerosene) |
| 0 | 50 | |
| 1 | 0.5 | Brown, fluffy solids |

The fact that Example 36 which produces no floc while Examples 38 and 40 produce heavy floc, all using the same RE 2000, can be explained by the fact that the electrodes used are "pre-corroded" one hour before the corrosion inhibitor is added at time zero. More severe or longer pre-corrosion places more iron salts in the water, which in turn produces heavier floc. The amount of iron in the system and/or the amount or type of floc do not adversely affect corrosion inhibition test results.

Many modifications may be made in the polyamines and dithiocarbamates thereof of the present invention without departing from their spirit and scope, which are defined only in the appended claims. For example, one skilled in the art may find that certain combinations of polyamine and polyepoxide reactants give particularly advantageous results. From the foregoing description, it will be seen that the inventive dithiocarbamates find particular use to clarify (by demulsification or flocculation) oil-in-water emulsions produced in oil and gas production. In addition, it is anticipated that the polyamine and/or dithiocarbamate derivatives thereof will find use as water clarifiers and/or corrosion inhibitors during oil, gas and natural gas production. The materials of the present invention will find addition uses as reverse emulsion breakers for these various applications.

We claim:

1. Polyamine compounds of the formula:

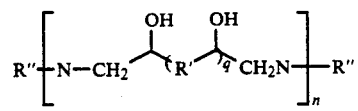

where R″ is independently selected from the group consisting of the structure —R—$NH_2$ and

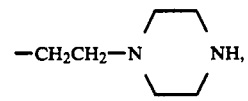

where R is independently selected from the group consisting of straight, branched or cyclic alkylene moieties and arylene moieties; and where R has from 1 to 26 carbon atoms; and where R' is —$(CH_2)_m$—O—R—O—$(CH_2)_m$— where n and m are independently range from 1 to 5 and q is 0 or 1.

2. Compounds of claim 1 wherein R' is

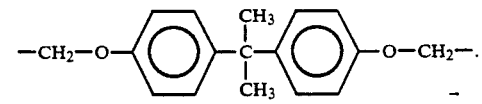

3. Compounds of claim 1 where R' is —$CH_2$—O—$CH_2CH_2$—O—$CH_2$—.

4. Polyamine compounds of the formula:

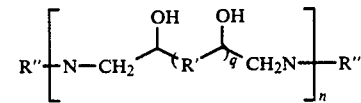

where R″ is independently selected from the group consisting of the structure —R—$NH_2$ and

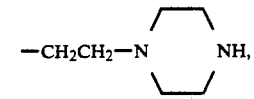

where R is independently selected from from the group consisting of —$(CH_2)_p$—,

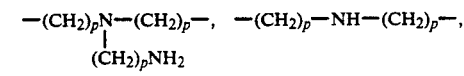

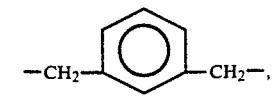

-continued

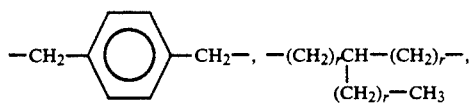

where p is from 1 to 8 and r is 0 to 8; and where R' is

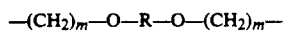

where n and m are independently range from 1 to 5 and q is 0 or 1.

5. Mixtures of polyamine compounds made by the reaction of a diamine selected from the group consisting of the formulae H₂NRNH₂,

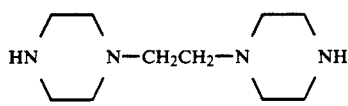

and mixtures thereof, and an epoxide selected from the group consisting of the formulae:

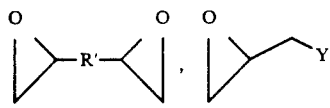

and mixtures thereof where R is independently selected from the group consisting of straight, branched or cyclic alkylene moieties and arylene moieties; and where R has from 1 to 26 carbon atoms; and where R' is

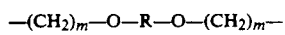

where m are independently 1 to 5, and the mole ratio of diamine to epoxide ranges from 1:1 to 100:1 and where Y is selected from the group consisting of Cl, Br, I, and O₃SR" and where R" is independently selected from the group consisting of the structure —R—NH₂ and

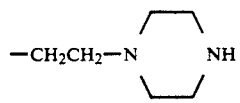

6. The mixtures of polyamine compounds of claim 5 where R' is

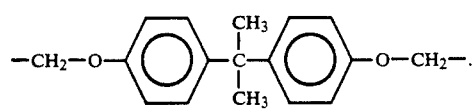

7. The mixtures of polyamine compounds of claim 5 where R' is

—CH₂—O—CH₂CH₂—O—CH₂—.

8. Mixtures of polyamine compounds made by the reaction of a diamine selected from the group consisting of the formulae H₂NRNH₂,

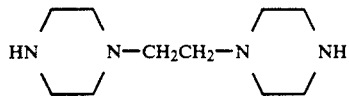

and mixtures thereof, and an epoxide selected from the group consisting of the formulae:

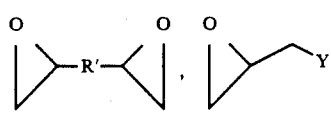

and mixtures thereof where R is independently selected from the group consisting of —(CH₂)$_p$—,

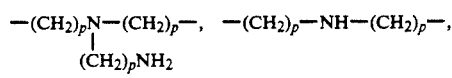

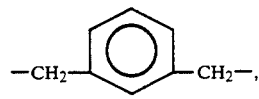

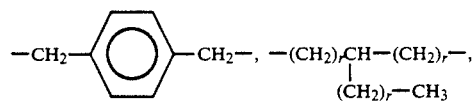

where p is from 1 to 8 and r is 0 to 8; and where R' is

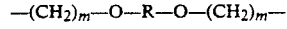

where m are independently 1 to 5, and the mole ratio of diamine to epoxide ranges from 1:1 to 100:1 and where Y is selected from the group consisting of Cl, Br, I, and O₃SR" and where R" is independently selected from the group consisting of the structure —R—NH₂ and

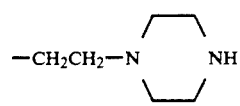

9. Dithiocarbamic salts of the formula:

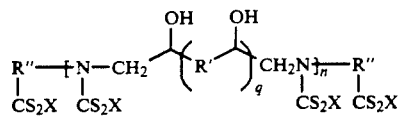

where R" is in dependently selected from the group consisting of the structure —R—NH₂ and

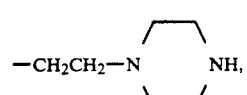

where R is independently selected from the group consisting of straight, branched or cyclic alkylene moieties and arylene moieties; and where R has from 1 to 26 carbon atoms; and where R' is
ti 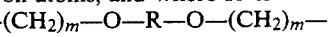

where n and m independently range from 1 to 5 and q is 0 or 1 and X is hydrogen, an alkali metal, an alkaline earth metal, ammonium ion or an amine.

10. The dithiocarbamic salts of claim 9 where R' is

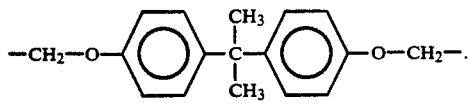

11. The dithiocarbamic salts of claim 9 where R' is —CH$_2$—O—CH$_2$CH$_2$—O—CH$_2$—.

12. Dithiocarbamic salts of the formula:

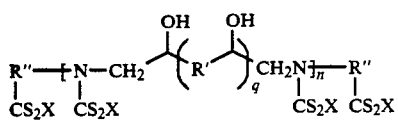

where R" is independently selected from the group consisting of the structure —R—NH$_2$ and

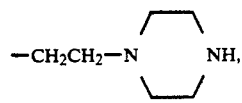

where R is independently selected from the group consisting of —(CH$_2$)$_p$—,

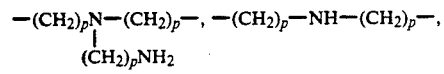

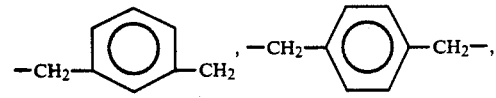

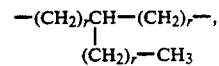

where p is from 1 to 8 and r is 0 to 8; and where R' is

—(CH$_2$)$_m$—O—R—O—(CH$_2$)$_m$— where n and m independently range from 1 to 5 and q is 0 or 1 and X is hydrogen, and alkali metal, an alkaline earth metal, ammonium ion or an amine.

13. A mixture of dithiocarbamic salts made by the process comprising the steps of:
reacting a diamine selected from the group consisting of the formulae H$_2$NRNH$_2$,

and mixtures thereof; and an epoxide selected from the group consisting of the formulae:

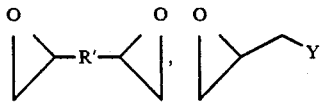

and mixtures thereof where R is independently selected from the group consisting of straight, branched or cyclic alkylene moieties and arylene moieties; and where R has from 1 to 26 carbon atoms; and where R' is —(CH$_2$)$_m$—O—R—O—(CH$_2$)$_m$— where m are independently 1 to 5, and the mole ratio of diamine to epoxide ranges form 1:1 to 100:1 and where Y is selected from the group consisting of Cl, Br, I, and O$_3$SR" and where R" is independently selected from the group consisting of the structure —R—NH$_2$ and

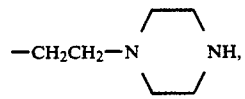

to give a polyamine intermediate;
reacting the polyamine intermediate with carbon disulfide, where the mole ratio of carbon disulfide to primary and secondary amine groups in the polyamine is about 1:1 to give a dithiocarbamic acid and
reacting the dithiocarbamic acid with a source of alkali metal ion, alkaline earth metal ion, ammonium ion amine ion to give a mixture of dithiocarbamic salts.

14. A method of clarifying an aqueous system containing an oil-in-water emulsion or dispersion of a non-aqueous discontinuous phase comprising the steps of:
contacting the aqueous system with an effective water clarifying amount of at least one dithiocarbamic salt of the formula:

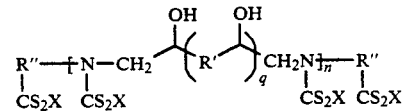

where R" is independently selected from the group consisting of the structure —R—NH$_2$ and

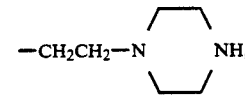

where R is independently selected from the group consisting of straight, branched or cyclic alkylene moieties and arylene moieties; and where R has from 1 to 26 carbon atoms; and where R' is —(CH$_2$)$_m$—O—R—O—(CH$_2$)$_m$— where n and m are independently 1 to 5 and q is 0 or 1 and X is hydrogen, an alkali metal an alkaline earth metal, ammonium ion or an amine; and maintaining the dithiocarbamic salt in the system for sufficient time to effectively clarify the aqueous system.

15. The method of claim 14 where in the dithiocarbamic salt R' is

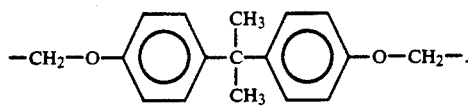

16. The method of claim 14 where in the dithiocarbamic salt where R' is —CH$_2$—O—CH$_2$CH$_2$—O—CH$_2$—.

17. A method of clarifying an aqueous system containing an oil-in-water emulsion or dispersion of a non-aqueous discontinuous phase comprising the steps of:
contacting the aqueous system with an effective water clarifying amount of at least one dithiocarbamic salt of the formula:

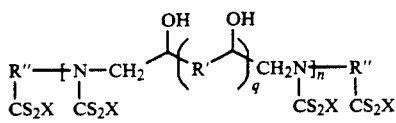

where R" is independently selected from the group consisting of the structure —R—NH$_2$ and

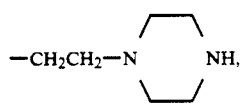

where R is independently selected from the group consisting of —(CH$_2$)$_p$—,

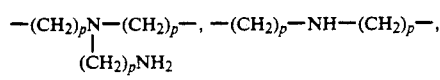

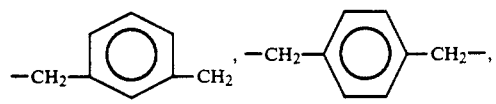

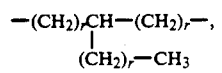

where p is from 1 to 8 and r is 0 to 8; and where R' is

—(CH$_2$)$_m$—O—R—O—(CH$_2$)$_m$— where n and m are independently 1 to 5 and q is 0 or 1 and X is hydrogen, an alkali metal an alkaline earth metal, ammonium ion or an amine; and maintaining the dithiocarbamic salt in the system for sufficient time to effectively clarify the aqueous system.

18. A method of clarifying an aqueous system containing an oil-in-water emulsion or dispersion of a non-aqueous discontinuous phase comprising the steps of:
contacting the aqueous system with an effective water clarifying amount of at least one dithiocarbamic salt made by the process comprising the steps of:
reacting a diamine selected from the group consisting of the formulae H$_2$NRNH$_2$,

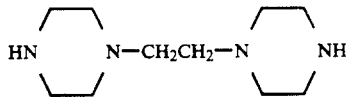

and mixtures thereof; and an epoxide selected from the group consisting of the formulae:

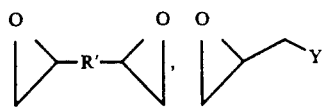

and mixtures thereof where R is independently selected from the group consisting of straight, branched or cyclic alkylene moieties and arylene moieties; and where R has from 1 to 26 carbon atoms; and where R' is —(CH$_2$)$_m$—O—R—O—(CH$_2$)$_m$— where m are independently 1 to 5, and the mole ratio of diamine to epoxide ranges from 1:1 to 100:1 and where Y is selected from the group consisting of Cl, Br, I, and O$_3$SR" and where R" is independently selected from the group consisting of the structure —R—NH$_2$ and

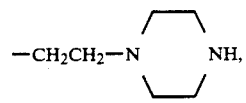

to give a polyamine intermediate;
reacting the polyamine intermediate with carbon disulfide, where the mole ratio of carbon disulfide to primary and secondary amine groups in the polyamine is about 1:1 to give a dithiocarbamic acid; and
reacting the dithiocarbamic acid with a source of alkali metal ion, alkaline earth metal ion, ammonium ion amine ion to give a dithiocarbamic salt; and
maintaining the dithiocarbamic salt in the system for sufficient time to effectively clarify the aqueous system 19. A method of inhibiting corrosion in an aqueous system comprising the steps of:
contacting the aqueous system with an effective corrosion inhibiting amount of at least one dithiocarbamic salt of the formula:

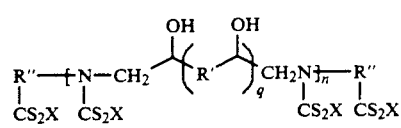

where R" is independently selected from the group consisting of the structure —R—NH$_2$ and

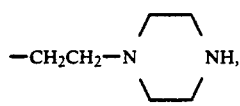

where R is independently selected from the group consisting of straight, branched or cyclic alkylene moieties and arylene moieties; and where R has from 1 to 26 carbon atoms; and where R' is

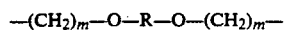

where n and m are independently 1 to 5 and q is 0 or 1 and X is hydrogen, an alkali metal an alkaline earth metal, ammonium ion or an amine; and maintaining the dithiocarbamic salt in the aqueous system for sufficient time to inhibit corrosion.

20. The method of claim 19 where in the dithiocarbamic salt R' is

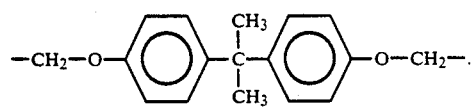

21. The method of claim 19 where in the dithiocarbamic salt where R' is $-CH_2-O-CH_2CH_2-O-CH_2-$.

22. A method of inhibiting corrosion in an aqueous system comprising the steps of:

contacting the aqueous system with an effective corrosion inhibiting amount of at least one dithiocarbamic salt of the formula:

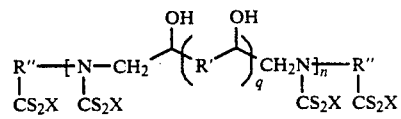

where R" is independently selected from the group consisting of the structure $-R-NH_2$ and

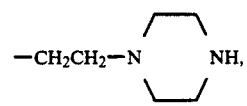

where R is independently selected from the group consisting of $-(CH_2)_p-$,

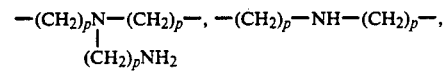

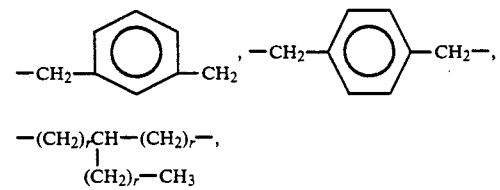

where p is from 1 to 8 and r is 0 to 8; and where R' is

where n and m are independently 1 to 5 and q is 0 or 1 and X is hydrogen, an alkali metal an alkaline earth metal ammonium ion or an amine; and maintaining the dithiocarbamic salt in the aqueous system for sufficient time to inhibit corrosion.

* * * * *

UNITED STATES PATENT AND TRADEMARK OFFICE
CERTIFICATE OF CORRECTION

PATENT NO. : 5,247,087
DATED : September 21, 1993
INVENTOR(S) : Gordon T. Rivers It is certified that error appears in the above-identified patent and that said Letters Patent is hereby corrected as shown below:

At column 20, line 68: please delete "ti".

At column 22, line 16: change "form" to "from".

Signed and Sealed this

Seventh Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,247,087
DATED : September 21, 1993
INVENTOR(S) : Gordon T. Rivers It is certified that error appears in the above-identified patent and that said Letters Patent is hereby corrected as shown below:

In the following locations, please delete the formula and substitute the formula below:

Abstract, line 8;
Column 5, line 14;
Column 6, line 9;
Column 18, line 6; and
Column 18, line 45:

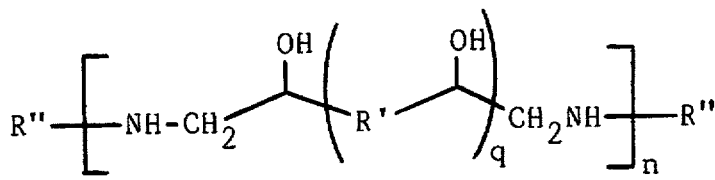

Signed and Sealed this

Twenty-second Day of July, 1997

Attest:

BRUCE LEHMAN

Attesting Officer

Commissioner of Patents and Trademarks